United States Patent
Qin et al.

(10) Patent No.: US 11,369,589 B2
(45) Date of Patent: Jun. 28, 2022

(54) MODULATOR OF INDOLEAMINE 2,3-DIOXYGENASE, PREPARATION METHOD AND USE THEREOF

(71) Applicants: NANJING CAREPHAR SHENGHUI PHARMACEUTICAL CO., LTD., Jiangsu (CN); JIANGSU CAREPHAR PHARMACEUTICAL CO., LTD., Jiangsu (CN)

(72) Inventors: Yinlin Qin, Jiangsu (CN); Mei Su, Jiangsu (CN); Min Ji, Jiangsu (CN); Haidong Liu, Jiangsu (CN); Xi Zong, Jiangsu (CN); Xianzhi Wu, Jiangsu (CN)

(73) Assignees: NANJING CAREPHAR SHENGHUI PHARMACEUTICAL CO., LTD., Nanjing (CN); JIANGSU CAREPHAR PHARMACEUTICAL CO., LTD., Nanjing (CN)

( * ) Notice: Subject to any disclaimer, the term of this patent is extended or adjusted under 35 U.S.C. 154(b) by 75 days.

(21) Appl. No.: 16/964,294

(22) PCT Filed: Jan. 22, 2019

(86) PCT No.: PCT/CN2019/072626
§ 371 (c)(1),
(2) Date: Jul. 23, 2020

(87) PCT Pub. No.: WO2019/144859
PCT Pub. Date: Aug. 1, 2019

(65) Prior Publication Data
US 2021/0030723 A1    Feb. 4, 2021

(30) Foreign Application Priority Data

Jan. 24, 2018 (CN) .......................... 201810067280.6
Jun. 7, 2018 (CN) .......................... 201810581413.1

(51) Int. Cl.
*A61K 31/4245* (2006.01)
*C07D 271/08* (2006.01)
*C07D 413/12* (2006.01)

(52) U.S. Cl.
CPC ........ *A61K 31/4245* (2013.01); *C07D 271/08* (2013.01); *C07D 413/12* (2013.01)

(58) Field of Classification Search
CPC ... A61K 31/424; C07D 271/08; C07D 413/12
See application file for complete search history.

(56) References Cited

FOREIGN PATENT DOCUMENTS

| CN | 102164902 | 8/2011 |
|---|---|---|
| WO | WO 2017044983 | 3/2017 |

OTHER PUBLICATIONS

Journal of International Pharmaceutical Research, Oct. 2008 by Yujian LV, Ning Zhou, Qingguo Meng.

*Primary Examiner* — Kamal A Saeed
(74) *Attorney, Agent, or Firm* — Gary J. Gershik

(57) ABSTRACT

The present invention relates to a modulator of 1,2,5-oxadiazole indoleamine-(2,3)-dioxygenase, a preparation method and use thereof, more particularly to compounds of Formula I and Formula II, an isomer thereof, a pharmaceutically acceptable salt or a pharmaceutically acceptable solvate thereof, and their use in preparing drugs for treating cancers, neurodegenerative diseases, eye diseases, mental disorders, depression, anxiety disorders, Alzheimer's diseases and/or autoimmune diseases. Specific meanings of R substituents in Formula I and Formula II are consistent with the description of the specification.

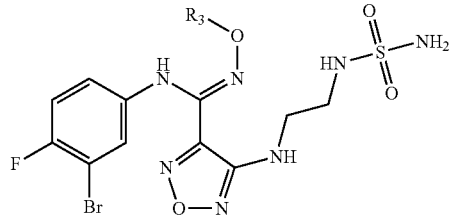

Formula I

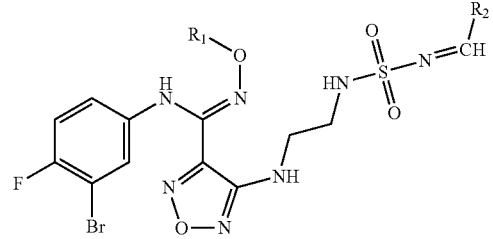

Formula II

10 Claims, No Drawings

MODULATOR OF INDOLEAMINE 2,3-DIOXYGENASE, PREPARATION METHOD AND USE THEREOF

RELATED APPLICATIONS

This application is a § 371 national stage of PCT International Application No. PCT/CN2019/072626, filed on Jan. 22, 2019, designating the United States and claiming priority of Chinese Application No. 201810581413.1, filed Jun. 7, 2018 and No. 201810067280.6, filed Jan. 24, 2018, the contents of each of which are hereby incorporated by reference into this application.

BACKGROUND

Technical Field

The present invention relates to a modulator of 1,2,5-oxadiazole indoleamine-(2,3)-dioxygenase, a preparation method and use thereof, sand belongs to the technical field of organic compound synthesis and medical application.

Related Art

Prodrug, also referred to as pro-drug, a drug precursor, a precursor drug and the like, refers to a compound which is obtained after chemical structure modification on drug, is inactive or less active in vitro, and release active drug through enzymatic or non-enzymatic conversion in vivo to achieve drug effects. At present, it has great effects on nervous system drugs, antitumor system drugs and antiviral drugs. The purpose of the prodrug is mainly to improve drug bioavailability, increase drug stability, reduce toxic and side effects, promote drug long-acting effects and the like. The prodrug is a very useful drug design method widely applied to administration route and dosage form design of various drug molecules. At present, clinically, the prodrug is not only used for improving lipophilicity of the drug to improve its transmembrane permeability, but also gradually used for improving water solubility of the drug. The prodrug has a great development space in tumor treatment. In summary, prodrug strategies have become an indispensable part of drug design and administration methods.

Tumors have specific tumor antigens, but in a natural state, the immune system sometimes cannot effectively control occurrence and development of the tumors. It is mainly because of immune tolerance to the tumor antigens in a tumor microenvironment, i.e. a specific non-responsive state of immunocompetent cells to tumor antigenic substances. Recent studies confirm that indoleamine-(2,3)-dioxygenase 1 (IDO1) is an initial and rate-limiting enzyme for catalyzing tryptophan metabolism along a kynurenine pathway outside human livers. Studies show that the IDO1 plays an important regulatory role in innate and adaptive immunity of a body by catalyzing the tryptophan metabolism. Abnormal tryptophan metabolism caused by overexpression of the IDO1 plays an important role in the immune tolerance of tumor patients. IDO1 expression is up-regulated in bodies of the tumor patients, and anti-tumor immunoreaction in the tumor microenvironment is inhibited through a series of complex mechanisms, promoting tumor angiogenesis. By inhibiting activity of IDO, the immune tolerance can be broken, and the anti-tumor immunoreaction can be enhanced. Therefore, an IDO pathway is one of key targets of tumor immunotherapy. Epacadostat, as an IDO inhibitor, is developed by Incyte Company and is used for treating cancers. The Epacadostat is in phase III clinical studies at present, and is used for treating cervical cancer, ovarian cancer, carcinoma tubae, peritoneal cancer, non-small cell lung cancer, triple negative breast cancer, urothelial cancer and other solid tumors.

However, it still needs to develop compounds with inhibitory activity on the IDO or with better pharmacodynamic performance in the art. The inventor found that an Epacadostat prodrug obtained by modifying active sites of the Epacadostat can improve the bioavailability of the Epacadostat. Therefore, the present invention is completed.

SUMMARY

Compounds of Formula I and Formula II, an isomer thereof, a pharmaceutically acceptable salt or a pharmaceutically acceptable solvate thereof are provided:

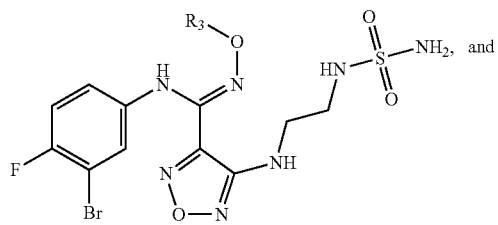

Formula I

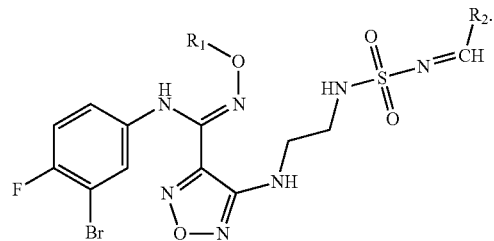

Formula II

R1 is selected from H, —C(=O)Ra, —C(=O)ORb, —C(=O)CnPhRc and —P(=O)(ORd)(ORe). Ra is independently selected from C1-C18 alkyl, haloalkyl, and carboxyl and cyanogroup substituted alkyl. Rb is independently selected from C1-C18 alkyl, haloalkyl, and carboxyl and cyanogroup substituted alkyl. Rc is independently selected from C1-C18 alkyl, haloalkyl. H and halogen. Rd and Re are selected from identical or different groups, and are each independently hydrogen, C1-C16 saturated or unsaturated chain hydrocarbyl, C1-C16 saturated or unsaturated cyclohydrocarbyl, aromatic ring or heteroaromatic ring. A substituent on the ring may be selected from halogen, nitryl, cyanogroup, hydroxyl, amino group, C1-C16 alkyl and C1-C16 alkoxy. n is 0 or 1.

R2 is selected from hydrogen, substituted or unsubstituted C1-C10 alkyl, substituted or unsubstituted C3-C10 cycloalkyl, substituted or unsubstituted C2-C10 alkenyl, substituted or unsubstituted C3-C10 alkynyl, substituted or unsubstituted C5-C20 aryl, and substituted or unsubstituted C3-C14 heteroaryl. Heteroatoms may be S, O, NH or NRf.

Rf and the "substituted" refer to having one or more of substituents selected from a group below: halogen, hydroxyl, —NH2, nitryl, —CN, substituted or unsubstituted C1-C10 alkyl, substituted or unsubstituted C1-C10 haloalkyl, substituted or unsubstituted C1-C10 alkoxy, substituted or unsubstituted C1-C10 cycloalkyl, substituted or unsubstituted C2-C10 alkenyl, substituted or unsubstituted C3-C10 alkynyl, substituted or unsubstituted C5-C20 aryl, and substituted or unsubstituted C3-C14 heteroaryl. Heteroatoms may be S. O and NH.

R3 is selected from —C(=O)Ra, —C(=O)ORb, —C(=O)CnPhRc and —P(=O)(ORd)(ORe). Ra is independently selected from C9-C18 alkyl, haloalkyl, and carboxyl and cyanogroup substituted alkyl. Rb is independently selected from C9-C18 alkyl, haloalkyl, and carboxyl and cyanogroup substituted alkyl. Rc is independently selected from C1-C18 alkyl, haloalkyl, H and halogen. Rd and Re are selected from identical or different groups, and are each independently hydrogen, C1-C16 saturated or unsaturated chain hydrocarbyl, C1-C16 saturated or unsaturated cyclohydrocarbyl, aromatic ring or heteroaromatic ring. A substituent on the ring may be selected from halogen, nitryl, cyanogroup, hydroxyl, amino group, C1-C16 alkyl and C1-C16 alkoxy. n is 0 or 1.

In another aspect, the present invention provides a pharmaceutical composition, including compounds of Formula I and/or Formula II, an isomer thereof, a pharmaceutically acceptable salt or a pharmaceutically acceptable solvate thereof according to claim 1, and a pharmaceutically acceptable carrier.

In another aspect, the present invention provides a preparation method of compounds of Formula I and Formula II. 1, according to a preparation method of the compound I, a compound 1 and a compound 2 are prepared into the compound of Formula I through a condensation dehydration reaction under a room temperature or heating condition in no solvent or an organic solvent.

According to a preparation method of the compound II, a compound 1 and a compound 3 are prepared into a compound of Formula 4 through a condensation dehydration reaction under a room temperature or heating condition in no solvent or an organic solvent. The compound of Formula 4 and a compound 5 are prepared into the compound of Formula II through a condensation dehydration reaction under a room temperature or heating condition in no solvent or an organic solvent.

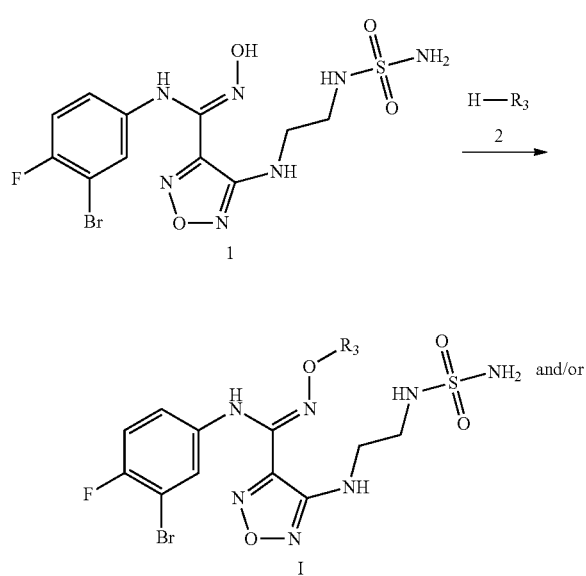

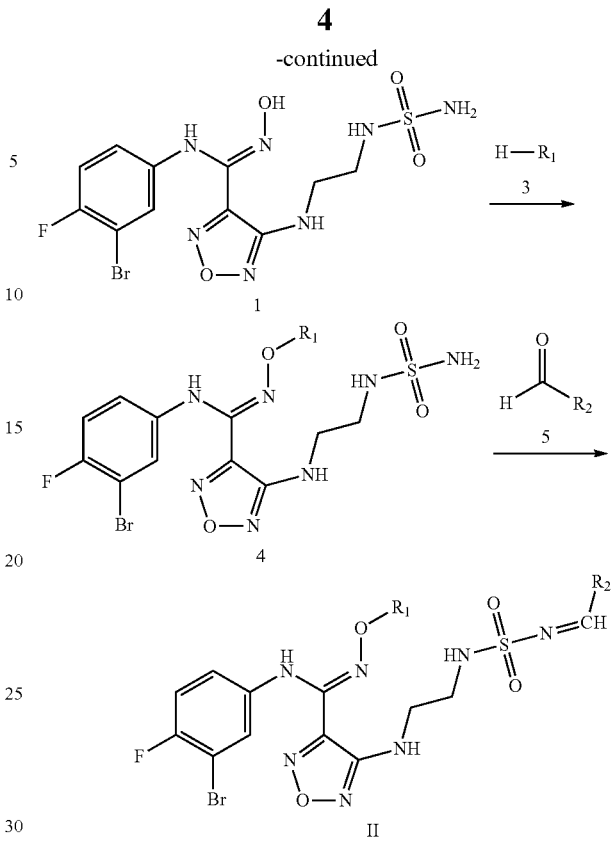

R1 is selected from H, —C(=O)Ra, —C(=O)ORb, —C(=O)CnPhRc, and —P(=O)(ORd)(ORe). Ra is independently selected from C1-C18 alkyl, haloalkyl, and carboxyl and cyanogroup substituted alkyl. Rb is independently selected from C1-C18 alkyl, haloalkyl, and carboxyl and cyanogroup substituted alkyl. Rc is independently selected from C1-C18 alkyl, haloalkyl. H and halogen. Rd and Re are selected from identical or different groups and are each independently hydrogen, C1-C16 saturated or unsaturated chain hydrocarbyl, C1-C16 saturated or unsaturated cyclohydrocarbyl, aromatic ring or heteroaromatic ring. A substituent on the ring may be selected from halogen, nitryl, cyanogroup, hydroxyl, amino group, C1-C16 alkyl and C1-C16 alkoxy. n is 0 or 1.

R2 is selected from hydrogen, substituted or unsubstituted C1-C10 alkyl, substituted or unsubstituted C3-C10 cycloalkyl, substituted or unsubstituted C2-C10 alkenyl, substituted or unsubstituted C3-C10 alkynyl, substituted or unsubstituted C5-C20 aryl, and substituted or unsubstituted C3-C14 heteroaryl. Heteroatoms may be S, O, NH or NRf.

Rf and the "substituted" refer to having one or a plurality of substituents selected from a group below: halogen, hydroxyl, —NH2, nitryl, —CN, substituted or unsubstituted C1-C10 alkyl, substituted or unsubstituted C1-C10 haloalkyl, substituted or unsubstituted C1-C10 alkoxy, substituted or unsubstituted C3-C10 cycloalkyl, substituted or unsubstituted C2-C10 alkenyl, substituted or unsubstituted C3-C10 alkynyl, substituted or unsubstituted C5-C20 aryl, and substituted or unsubstituted C3-C14 heteroaryl. Heteroatoms may be S, O and NH.

R3 is selected from —C(=O)Ra, —C(=O)ORb, —C(=O)CnPhRc, and —P(=O)(ORd)(ORe). Ra is independently selected from C9-C18 alkyl, haloalkyl, and carboxyl and cyanogroup substituted alkyl. Rb is independently selected from C9-C18 alkyl, haloalkyl, and carboxyl and cyanogroup substituted alkyl. Rc is independently selected from C1-C18 alkyl, haloalkyl, H and halogen. Rd and Re are selected from identical or different groups and are each independently hydrogen, C1-C16 saturated or unsaturated chain hydrocarbyl, C1-C16 saturated or unsaturated cyclohydrocarbyl, aromatic ring or heteroaromatic ring. A substituent on the ring may be selected from halogen, nitryl, cyanogroup, hydroxyl, amino group, C1-C16 alkyl and C1-C16 alkoxy. n is 0 or 1.

The selected solvent is selected from one or more of methyl alcohol, ethyl alcohol, dichloromethane, trichloromethane, acetonitrile, DMF, DMA, DMSO, THF and toluene, including but not limited to the above solvents.

A reaction temperature ranges from 0° C. to 200° C.

Reference may be made to embodiments for the above specific reaction conditions.

In another aspect, the present invention provides compounds of Formula I and Formula II, an isomer thereof, a pharmaceutically acceptable salt or a pharmaceutically acceptable solvate thereof or use of a pharmaceutical composition according to claim 5 in preparing an indoleamine-(2,3)-dioxygenase inhibitor, or a use in preparing drugs for preventing and/or treating indoleamine-(2.3)-dioxygenase-mediated diseases, or use in preparing anti-inflammatory drugs.

The indoleamine-(2,3)-dioxygenase-mediated diseases are cancers, neurodegenerative diseases, eye diseases, mental disorders, depression, anxiety disorders, Alzheimer's diseases and/or autoimmune diseases.

In an embodiment of the present invention, when R1 is selected from H a compound of General Formula II, an isomer thereof, a pharmaceutically acceptable salt or a pharmaceutically acceptable solvate thereof are as follows:

General Formula II

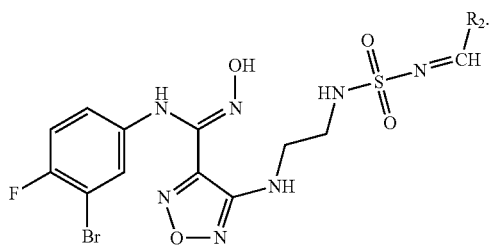

R2 is selected from hydrogen, and substituted or unsubstituted $C_1$-$C_{10}$ alkyl, including but not limited to methyl, ethyl, n-propyl, isopropyl, n-butyl, etc.; substituted or unsubstituted $C_3$-$C_{10}$ cycloalkyl, including but not limited to cyclopropyl, cyclopentyl, cyclohexyl, etc.; substituted or unsubstituted $C_2$-$C_{10}$ alkenyl, including but not limited to ethenyl, propenyl, butenyl, etc.; substituted or unsubstituted $C_3$-$C_{10}$ alkynyl, including but not limited to propinyl, butynyl, etc.; substituted or unsubstituted $C_5$-$C_{20}$ aryl, including but not limited to phenyl, tolyl, methoxyphenyl, naphthyl, etc.; and substituted or unsubstituted $C_3$-$C_{14}$ heteroaryl. Heteroatoms may be S, O, NH or $NR_f$, including but not limited to thiofuran, furfuran, pyran, pyrrole, pyridine, pyridazine, etc.

$R_f$ and the "substituted" refer to having one or more of substituents selected from a group below: halogen, hydroxyl, —$NH_2$, nitryl, —CN, and substituted or unsubstituted $C_1$-$C_{10}$ alkyl, including but not limited to methyl, ethyl, n-propyl, isopropyl, n-butyl, etc.; substituted or unsubstituted $C_1$-$C_{10}$ haloalkyl, including but not limited to fluoro/chloro/bromo/iodo methyl, fluoro/chloro/bromo/iodo ethyl, fluoro/chloro/bromo/iodo n-propyl, fluoro/chloro/bromo/iodo isopropyl, fluoro/chloro/bromo/iodo n-butyl, etc.; substituted or unsubstituted $C_1$-$C_{10}$ alkoxy, including but not limited to methoxyl, ethyoxyl, propoxyl, butoxyl, etc.; substituted or unsubstituted $C_1$-$C_{10}$ cycloalkyl, including but not limited to cyclopropyl, cyclopentyl, cyclohexyl, etc.; substituted or unsubstituted $C_1$-$C_{10}$ alkenyl, including but not limited to ethenyl, propenyl, butenyl, etc.; substituted or unsubstituted $C_3$-$C_{10}$ alkynyl, including but not limited to propinyl, butynyl, etc.; substituted or unsubstituted $C_5$-$C_{20}$ aryl, including but not limited to phenyl, tolyl, methoxyphenyl, naphthyl, etc.; and substituted or unsubstituted $C_3$-$C_{14}$ heteroaryl. Heteroatoms may be S, O, NH or $NR_2$, including but not limited tothiofuran, furfuran, pyran, pyrrole, pyridine, pyridazine, etc.

In another aspect, the present invention provides a pharmaceutical composition, including a compound of General Formula II, an isomer thereof or a pharmaceutically acceptable salt or a pharmaceutically acceptable solvate thereof when R1 is selected from H. It includes but is not limited to alkali metal used by alkali addition salt, such as sodium, potassium, calcium, magnesium, etc. It includes but not limited to organic acid or inorganic acid used by alkali addition salt. The organic acid is, for example, formic acid, acetic acid, propionic acid, propandioic acid, methanesulfonic acid, oxalic acid, trifluoroacetic acid, lactic acid, tartaric acid, citric acid, maleic acid, fumaric acid, benzoic acid, benzene methane sulfonic acid, gluconic acid, succinic acid, salicylic acid and malic acid. The inorganic acid is, for example, hydrochloric acid, hydrobromic acid, sulfuric acid and phosphoric acid.

In another aspect, the present invention provides a preparation method of the compound of Formula II. A compound of Formula 2 and a compound of Formula 3 are prepared into the compound of Formula II through a condensation dehydration reaction in no solvent or an organic solvent.

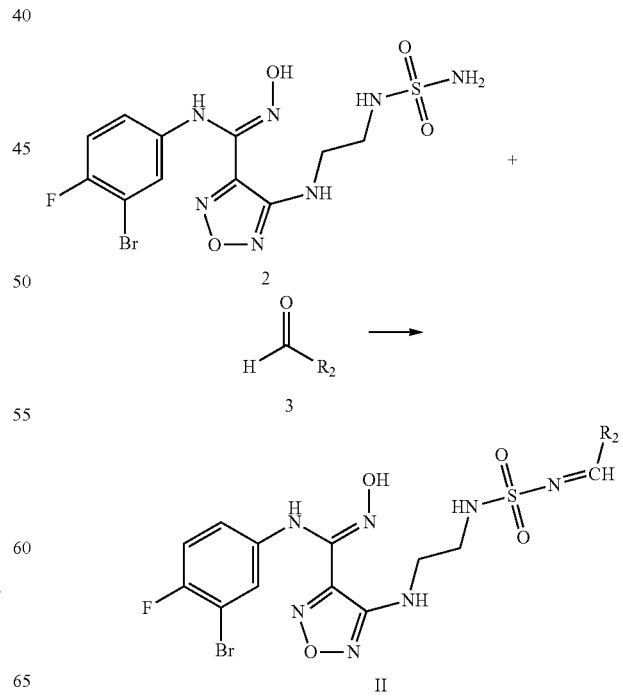

R2 is selected from hydrogen, substituted or unsubstituted $C_1$-$C_{10}$ alkyl, substituted or unsubstituted $C_3$-$C_{10}$ cycloalkyl, substituted or unsubstituted $C_2$-$C_{10}$ alkenyl, substituted or unsubstituted $C_3$-$C_{10}$ alkynyl, substituted or unsubstituted $C_5$-$C_{20}$ aryl, and substituted or unsubstituted $C_3$-$C_{14}$ heteroaryl. Heteroatoms may be S, O, NH or $NR_f$.

$R_f$ and the "substituted" refer to having one or more of substituents selected from a group below: halogen, hydroxyl, —$NH_2$, nitryl, —CN, substituted or unsubstituted $C_1$-$C_{10}$ alkyl, substituted or unsubstituted $C_1$-$C_{10}$ haloalkyl, substituted or unsubstituted $C_1$-$C_{10}$ alkoxy, substituted or unsubstituted $C_1$-$C_{10}$ cycloalkyl, substituted or unsubstituted $C_2$-$C_{10}$ alkenyl, substituted or unsubstituted $C_3$-$C_{10}$ alkynyl, substituted or unsubstituted $C_5$-$C_{20}$ aryl, and substituted or unsubstituted $C_3$-$C_{14}$ heteroaryl. Heteroatoms may be S, O or NH.

The selected solvent is selected from one or more of methyl alcohol, ethyl alcohol, dichloromethane, trichloromethane, acetonitrile, DMF, DMA, DMSO, THF and toluene, including but not limited to the above solvents.

A reaction temperature ranges from 0° C. to 200° C.

Reference may be made to embodiments for the above specific reaction conditions.

In another aspect, the present invention provides use of a compound of Formula II or a pharmaceutically acceptable salt thereof according to claim 1, in (1) preparing an indoleamine-(2,3)-dioxygenase inhibitor, (2) preparing drugs for preventing and/or treating indoleamine-(2,3)-dioxygenase-mediated diseases, and (3) preparing anti-inflammatory drugs.

The indoleamine-(2,3)-dioxygenase-mediated diseases are cancers, neurodegenerative diseases, eye diseases, mental disorders, depression, anxiety disorders, Alzheimer's diseases and/or autoimmune diseases.

Beneficial effects: the present invention has the following advantages that an Epacadostat prodrug compound designed and obtained by the present invention can be fast converted into original drug Epacadostat. Additionally, compared with the original drug, the obtained prodrug compound has better solubility and higher bioavailability, and enhances the pharmaceutical effects.

DETAILED DESCRIPTION

The following further describes the present invention with reference to specific embodiments. These embodiments are merely intended to explain and describe, but are not intended to limit the scope and essence of the present invention.

$^1$H-NMR was determined by a WNMR-I-400/500 MHz instrument. MS was determined by an Agilent1100LC/MS instrument. Used reagents including dichloromethane, acetonitrile and the like were all purchased from Energy Chemical Reagent Company. Deuterated DMSO was purchased from J&K Chemical Reagent Company. All solvents were redistilled before use. Used anhydrous solvents were all obtained through drying treatment according to a standard method. Product purification all adopted a silica gel (200 to 300 meshes) column chromatography method unless otherwise stated. Silica gel (200 to 300 meshes) was produced by Qingdao Haiyang Chemical Company. Thin silica gel plates were produced by Yantai Jiangyou Silica Gel Development Co., Ltd.

Embodiment 1 Synthesis of Compound of Formula I-1

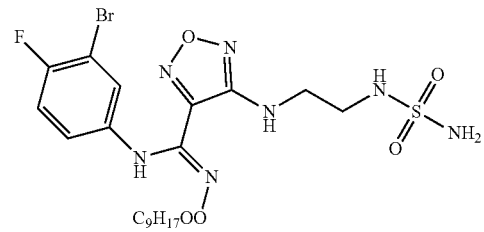

159 mg of nonanoic acid, 162 mg of N,N'-carbonyldiimidazole (CDI) and 3 mL of THF were added into a reaction bottle. After stirring reaction at 60° C. for 1 h, THF (4 mL) solution of 306 mg EPA-P was added into the reaction bottle. Reaction was further performed for 2 h. TLC was adopted for monitoring the reaction (EA:PE=1:1 or DCM:methyl alcohol=10:1). The reaction was completed. A temperature of reaction liquid was lowered to a room temperature. Silica gel was added for sample mixing. Products were separated by column chromatography (with eluent EA:PE=1:3, a target compound was obtained through elution). 210 mg of white solid was obtained. The yield was 36.4%. MS m/z: 578.1 (M+1)$^+$. $^1$HNMR (400 MHz, DMSO) δ 9.70-9.84 (d, 1H), 7.39-7.6 (m, 2H). 6.50-7.10 (m, 5H), 3.32 (s, 1H), 3.12 (m, 2H), 2.31 (m, 2H), 1.53 (m, 2H), 1.25 (m, 10H), 0.88 (m, 6H).

Embodiment 2 Synthesis of Compound of Formula I-2

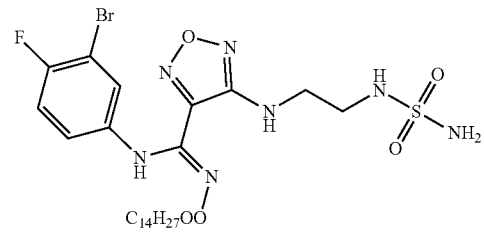

228 mg of myristic acid, 162 mg of N,N'-carbonyldiimidazole (CDI) and 3 mL of THF were added into a reaction bottle. After stirring reaction at 60° C. for 1 h, THF (4 mL) solution of 306 mg EPA-P was added into the reaction bottle. Reaction was further performed for 2 h. TLC was adopted for monitoring the reaction (EA:PE=1:1 or DCM:methyl alcohol=10:1). The reaction was completed. A temperature of reaction liquid was lowered to a room temperature. Silica gel was added for sample mixing. Products were separated by column chromatography (with eluent EA:PE=1:3, a target compound was obtained through elution). 270 mg of white solid was obtained. The yield was 42.9%. MS m/z: 648.2 (M+1)$^+$. $^1$HNMR (400 MHz, DMSO) δ 9.70-9.84 (d, 1H), 7.39-7.6 (m, 2H), 6.50-7.10 (m, 5H), 3.12 (s, 1H), 3.05 (m, 2H), 2.35 (m, 2H), 1.45 (m, 2H), 1.23 (m, 20H), 0.83 (m, 6H).

Embodiment 3 Synthesis of Compound of Formula II-1

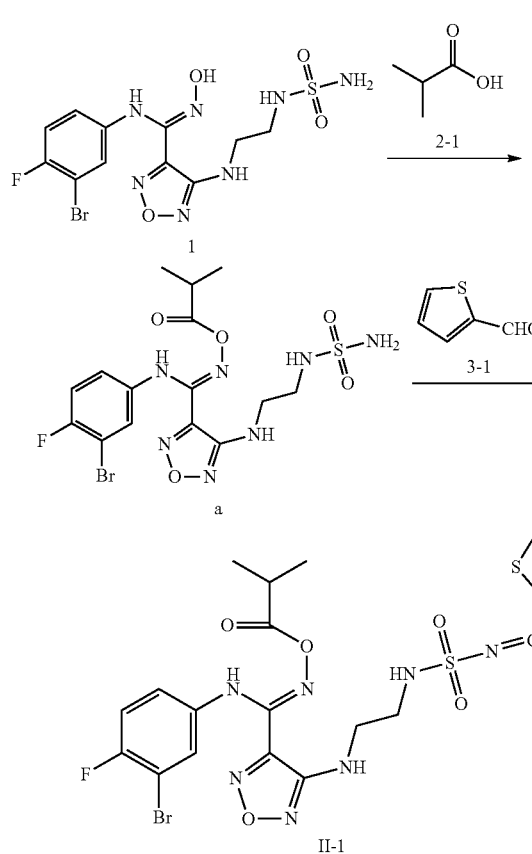

264 mg of compound of Formula 2-1, 486 mg of N,N'-carbonyldiimidazole (CDI) and 8 mL of THF were added into a reaction bottle. After stirring reaction at 60° C. for 1 h, THF (8 mL) solution of 876 mg compound of Formula I was added into the reaction bottle. Reaction was further performed for 2 h. TLC was adopted for monitoring the reaction. The reaction was completed. A temperature of reaction liquid was lowered to a room temperature. Silica gel was added for sample mixing. Target products were separated by column chromatography (eluent EA:PE=1:3). 400 mg of white solid compound of Formula a was obtained. The yield was 39.56%.

The obtained compound of Formula a was added into a reaction tube. 0.5 mL of compound of Formula 3-1 was added. Stirring was started. A temperature was raised to 110° C. Reaction was performed for 1 h. TLC was adopted for detecting the reaction. The reaction was completed. A temperature of reaction liquid was lowered to a room temperature. Ethyl acetate was added for dissolved clarification. Silica gel was added for sample mixing. Target products were separated by column chromatography (eluent EA:PE=1:5). 170 mg of yellow solid compound of Formula II-1 was obtained. The yield was 35.83%. MS m/z: 603.5 (M+1)$^+$. $^1$H NMR (400 MHz, DMSO) δ 9.75 (d, 1H), 9.07 (d, 1H), 8.15-8.03 (m, 2H), 7.77 (m, 1H), 7.65-7.53 (m, 1H), 7.44-6.99 (m, 3H), 6.77 (m. 1H), 3.31 (m, 1H), 3.10 (m, 2H), 2.59-2.45 (m, 2H), 1.02 (m, 6H).

Embodiment 4 Synthesis of Compound of Formula II-2

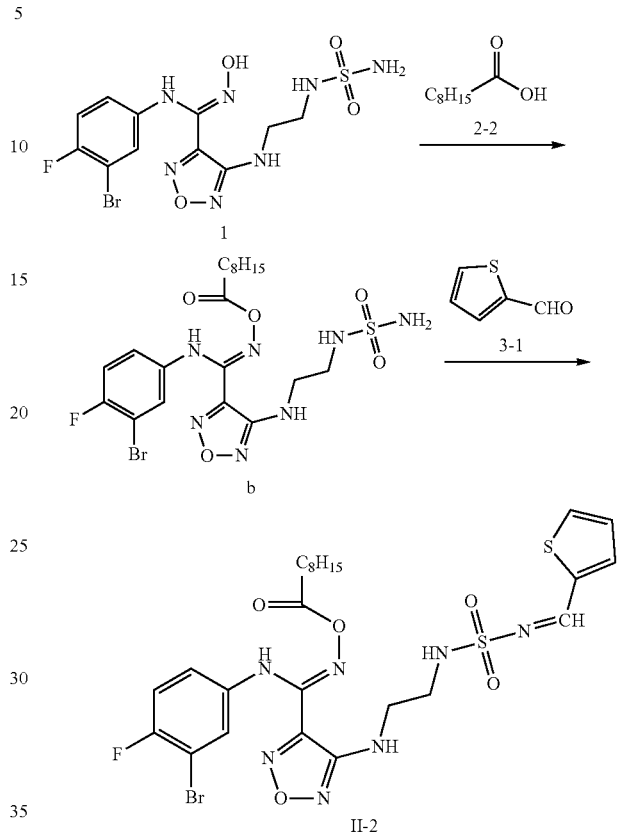

464 mg of compound of Formula 2-2, 786 mg of N,N'-carbonyldiimidazole (CDI) and 8 mL of THF were added into a reaction bottle. After stirring reaction at 60° C. for 1 h, THF (8 mL) solution of 800 mg compound of Formula I was added into the reaction bottle. Reaction was further performed for 2 h. TLC was adopted for monitoring the reaction. The reaction was completed. A temperature of reaction liquid was lowered to a room temperature. Silica gel was added for sample mixing. Target products were separated by column chromatography (eluent EA:PE=1:3). 443 mg of white solid compound of Formula b was obtained. The yield was 42.10%.

The obtained compound of Formula b was added into a reaction tube. 0.5 mL of compound of Formula 3-1 was added. Stirring was started. A temperature was raised to 110° C. Reaction was performed for 1 h. TLC was adopted for detecting the reaction. The reaction was completed. A temperature of reaction liquid was lowered to a room temperature. Ethyl acetate was added for dissolved clarification. Silica gel was added for sample mixing. Target products were separated by column chromatography (eluent EA:PE=1:5). 180 mg of yellow solid compound of Formula II-2 was obtained. The yield was 34.96%. MS m/z: 659.7 (M+1)$^+$. $^1$H NMR (400 MHz, DMSO) δ 9.76 (d, 1H), 9.07 (d, 1H), 8.16-8.03 (m, 2H), 7.79 (m, 1H). 7.59 (m, 1H), 7.44-7.01 (m, 3H), 6.74 (m, 1H). 3.33 (m, 2H), 3.10 (m, 21), 2.30 (m, 2H), 1.56-1.36 (m, 211), 1.32-1.14 (m, 81), 0.84 (m, 3H).

Embodiment 5 Synthesis of Compound of Formula II-3

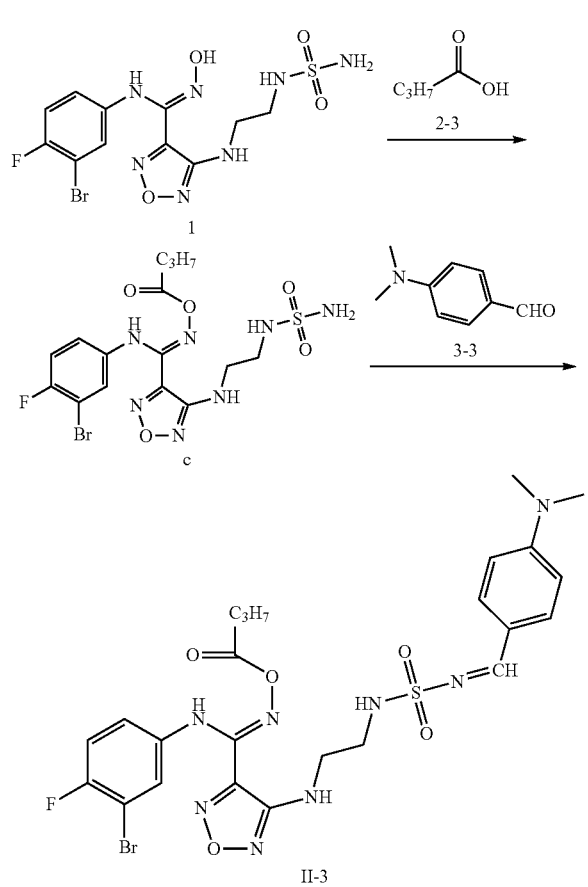

Embodiment 6 Synthesis of Compound of Formula II-4

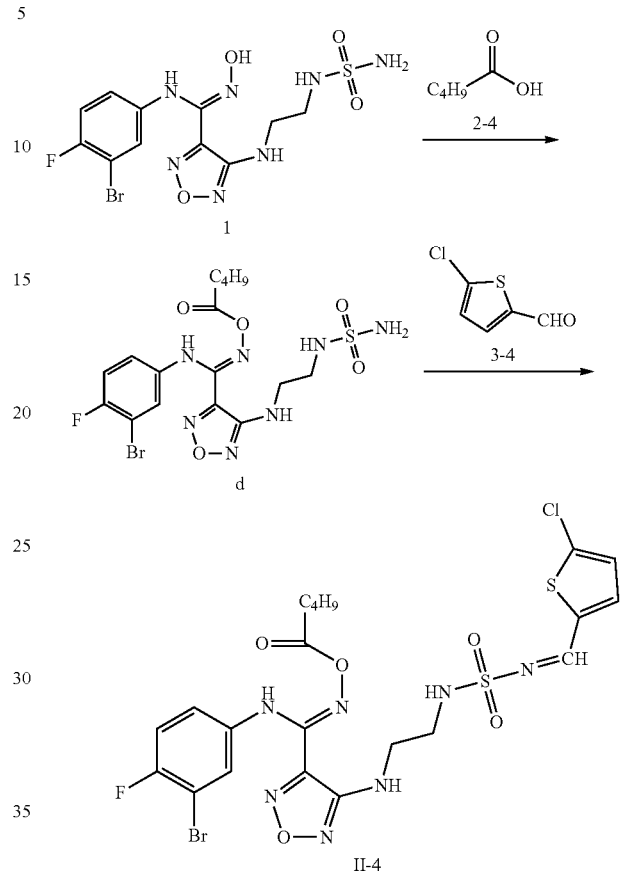

464 mg of compound of Formula 2-3, 800 mg of N,N'-carbonyldiimidazole (CDI) and 8 mL of THF were added into a reaction bottle. After stirring reaction at 60° C. for 1 h, THF (8 mL) solution of 800 mg compound of Formula I was added into the reaction bottle. Reaction was further performed for 2 h. TLC was adopted for monitoring the reaction. The reaction was completed. A temperature of reaction liquid was lowered to a room temperature. Silica gel was added for sample mixing. Target products were separated by column chromatography (eluent EA:PE=1:3). 353 mg of white solid compound of Formula c was obtained. The yield was 38.04%.

The obtained compound of Formula c was added into a reaction tube. 0.5 mL of compound of Formula 3-3 was added. Stirring was started. A temperature was raised to 110° C. Reaction was performed for 1 h. TLC was adopted for detecting the reaction. The reaction was completed. A temperature of reaction liquid was lowered to a room temperature. Ethyl acetate was added for dissolved clarification. Silica gel was added for sample mixing. Target products were separated by column chromatography (eluent EA:PE=1:5). 189 mg of yellow solid compound of Formula II-3 was obtained. The yield was 42.56%. MS m/z: 640.6 (M+1)$^+$. $^1$HNMR (400 MHz, DMSO) δ 9.75 (d, 1H), 8.65 (d, J=6.3 Hz, 1H), 7.77 (m, 2H), 7.47 (t, 1H), 7.44-7.34 (m, 1H), 7.26 (t, 1H), 6.99 (m, 1H), 6.79 (d, 2H), 6.57 (t, 1H), 3.32-3.28 (m, 2H), 3.10-3.01 (m, 8H), 2.29 (m, 2H), 1.61-1.38 (m, 2H), 0.93-0.75 (m, 3H).

464 mg of compound of Formula 2-4, 800 mg of N,N'-carbonyldiimidazole (CDI) and 8 mL of THF were added into a reaction bottle. After stirring reaction at 60° C. for 1 h, THF (8 mL) solution of 800 mg compound of Formula I was added into the reaction bottle. Reaction was further performed for 2 h. TLC was adopted for monitoring the reaction. The reaction was completed. A temperature of reaction liquid was lowered to a room temperature. Silica gel was added for sample mixing. Target products were separated by column chromatography (eluent EA:PE=1:3). 353 mg of white solid compound of Formula d was obtained. The yield was 37.02%.

The obtained compound of Formula d was added into a reaction tube. 0.5 mL of a compound of Formula 3-4 was added. Stirring was started. A temperature was raised to 110° C. Reaction was performed for 1 h. TLC was adopted for detecting the reaction. The reaction was completed. A temperature of reaction liquid was lowered to a room temperature. Ethyl acetate was added for dissolved clarification. Silica gel was added for sample mixing. Target products were separated by column chromatography (eluent EA:PE=1:5). 203 mg of yellow solid compound of Formula II-4 was obtained. The yield was 46.15%. MS m/z: 651.8 (M+1)$^+$. $^1$HNMR (400 MHz, DMSO) δ 9.76 (d, 1H), 8.99 (d, 1H), 7.99 (m, 1H), 7.84 (m, 1H), 7.45-7.34 (m, 2H), 7.27 (t, 1H), 7.06-6.96 (m, 1H), 6.74 (m, 1H), 3.31 (m, 2H), 3.08 (m, 2H), 2.30 (m, 2H), 1.50 (m, 4H), 0.85 (m, 3H).

Embodiment 7 In Vitro Plasma Experiment of Target Compounds 7.1 Determination Conditions of High Performance Liquid Chromatography Liquid chromatograph: Waters 2489UV/Visible Detector, Waters 1525BinaryHPLC Pump.

Chromatographic column: Kromasil 100-5-$C_{18}$, Dim: 4.6×150 mm, Part/Serial: M05CLA15/E121514.

Mobile phase: acetonitrile (50% to 80%) and water gradient elution.

Flow rate: 1 mL/min at a column temperature of 25° C.
Detection wavelength: 254 nm at a sample size of 10 μL.
Under the condition of no mobile phase interference, the Epacadostat retention time was about 20 min.

7.2 Sample Preparation

The target compounds were dissolved into a DMSO solvent. The concentration was converted into Epacadostat 120 mg/mL according to the concentration. 20 μL of the solution was taken and added into 1.18 mL of fresh rat blank plasma, and incubation was carried out at 37° C. to obtain a sample.

7.3 Sample Pretreatment

120 μL of the sample was precisely sucked at a specified time point each time. 120 μL of acetonitrile was added. High-speed vortex mixing was performed for 2 min. Centrifugation was performed at 10000 r/min for 15 min. Supernatant was taken and filtered by a 13 mm 0.45 μm filter membrane, and then determination could be performed.

7.4 Original Drug Epacadostat Plasma Stability Test

20 μL of DMSO solution (120 mg/mL) of Epacadostat was taken and added into 1.18 mL of fresh rat blank plasma. Incubation was performed at 37° C. 120 μL of sample was taken at different time points respectively. Sample pretreatment was performed according to the method of 7.3. Determination was performed by an HPLC method. A peak area was recorded, and a drug concentration was calculated. The results are as shown in Table 1.

TABLE 1

|  | Time/h | | | |
| --- | --- | --- | --- | --- |
|  | 1 | 3 | 6 | 24 |
| Epacadostat concentration in plasma (mg/mL) | 1.22 | 1.20 | 1.24 | 1.20 |

The data in Table 1 show that the Epacadostat can stably exist in the plasma.

7.5 In Vitro Plasma Conversion Experiment of Target Compounds

According to the method of 7.4, we performed in vitro plasma conversion experiment on the target compounds to test conversion rates of the compounds converted into the Epacadostat at different time points. The results are as shown in Table 2.

TABLE 2

| Compound | Conversion rate at different time points (%) | | | | | |
| --- | --- | --- | --- | --- | --- | --- |
|  | 0.5 h | 1 h | 2 h | 3 h | 6 h | 12 h |
| I-1 | 59.8 | 64.8 | 65.5 | 72.4 | 88.8 | 98.9 |
| I-2 | 46.2 | 5.3 | 67.9 | 87.2 | 91.0 | 100 |
| II-1 | 33.7 | 56.3 | 77.2 | 87.2 | 93.8 | 100 |
| II-2 | 43.2 | 66.3 | 81.2 | 90.2 | 97.2 | 100 |

TABLE 2-continued

| Compound | Conversion rate at different time points (%) | | | | | |
| --- | --- | --- | --- | --- | --- | --- |
|  | 0.5 h | 1 h | 2 h | 3 h | 6 h | 12 h |
| II-3 | 31.1 | 43.1 | 58.3 | 70.3 | 88.3 | 98.3 |
| II-4 | 47.2 | 49.0 | 51.6 | 75.2 | 89.6 | 100 |

The data above show that all of the target compounds can be fast converted into original drug Epacadostat in the plasma.

Embodiment 8 Rat In Vivo Pharmacokinetic Experiment 15 healthy SD male rats with the body weight in a range of 200 to 220 g were taken, and were regularly fed with rat standard formula granulated feed every day. Fasting was performed for 12 h before the experiment. Feeding was resumed 4 h after administration. Free water drinking was allowed before, after and during the experiment. The rats were randomly divided into 6 groups. The first group was fed with Epacadostat at single dose. The second to sixth groups were fed with compounds prepared according to Embodiment 1 to Embodiment 5 at single dose. The molar concentration of Epacadostat in the dosage of administration of the 6 groups of rats was 10 mg/kg. 0.2 to 0.3 mL of blood was taken from fundus venous plexus before administration (at 0 h), and 0.5, 1, 2, 4, 6, 8, 10, 24 and 48 h after administration respectively. Heparin anticoagulation was performed. The plasma was separated through centrifugation. 0.1 mL of plasma was accurately measured and added into an EP tube. 1.2 mL of ethyl acetate was added. High-speed uniform mixing was performed by a vortex mixer for 5 min. Centrifugation was performed for 5 min (8000 r/min). Supernatant was collected. A solvent was blown dry by nitrogen gas on a pressure blowing concentrator at 30° C. Residues were dissolved by 100 μL of mobile phase. High-speed uniform mixing was performed by the vortex mixer for 10 min. Centrifugation was performed for 5 min (14000 r/min). 80 μL of supernatant was transferred into a sample bottle. 10 μL of the sample was detected through HPLC. A chromatogram map was recorded. The results are as shown in Table 3:

TABLE 3

| Compound | Oral bioavailability (AUC, μL · h) |
| --- | --- |
| Epacadostat | 15.1 |
| I-1 | 14.7 |
| I-2 | 14.2 |
| II-1 | 17.4 |
| II-2 | 16.9 |
| II-3 | 15.8 |
| II-4 | 16.1 |

In vivo and in vitro pharmacological experiments show that the Epacadostat prodrug compound obtained by the design method of the present invention can be effectively converted into Epacadostat in the plasma under the action of enzymes. In vivo studies show that the compound has good bioavailability, is superior to the Epacadostat, and has further clinic study potentials as a novel IDO inhibitor.

Embodiment 9 Synthesis of Compound of Formula II-5

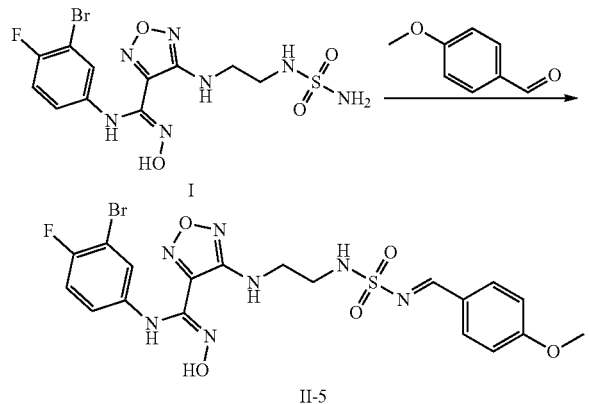

400 mg (0.92 mmol) of compound of Formula I and 0.68 g (5.0 mmol) of p-anisaldehyde were added into a reaction bottle. Stirring was started. A temperature was raised to 110° C. Reaction was performed for 1 h. TLC was adopted for monitoring the reaction (EA:PE=1:1). The reaction was completed. A temperature of reaction liquid was lowered to a room temperature. The reaction liquid was cooled into solid. Ethyl acetate was added for dissolving the solid. Silica gel was added for sample mixing. Products were separated by column chromatography (raw material aldehyde was firstly eluted out by an eluent EA:PE=1:10, and then target compounds were eluted out by EA:PE=1:2). 265 mg of yellow solid was obtained. MS m/z: 557.8 (M+1)$^+$. $^1$H-NMR (400 MHz, DMSO-d$_6$) δ: 11.47 (s, 1H), 8.85 (s, 2H), 7.97 (d, J=8.8 Hz, 2H), 7.73 (s, 1H), 7.21~7.05 (m, 4H), 6.82~6.71 (m, 1H), 6.27 (t, J=6.0 Hz, 1H), 3.86 (s, 3H), 3.40-3.36 (m, 2H), 3.23~3.09 (m, 2H).

Embodiment 10 Synthesis of Compound of Formula II-6

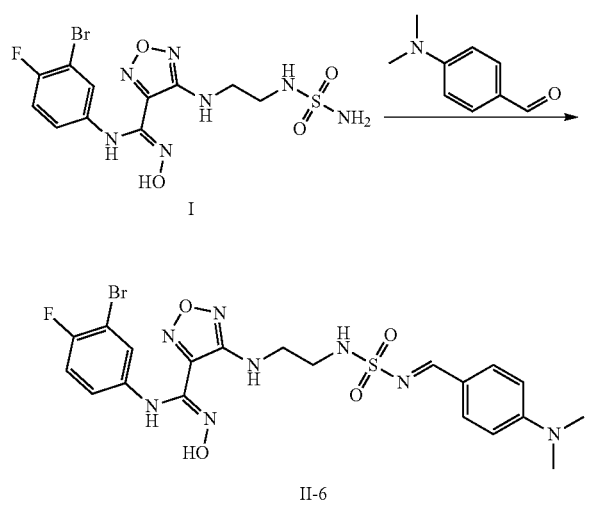

400 mg (0.92 mmol) of compound of Formula I and 0.75 g (5.0 mmol) of p-dimethylaminobenzaldehyde were added into a reaction bottle. 10 mL of dichloromethane was added. Stirring was started. A temperature was raised to 30° C. Reaction was performed for 1 h. TLC was adopted for monitoring the reaction (EA:PE=1:1). The reaction was completed. A temperature of reaction liquid was lowered to a room temperature. The reaction liquid was cooled into solid. Ethyl acetate was added for dissolving the solid. Silica gel was added for sample mixing. Products were separated by column chromatography (raw material aldehyde was firstly eluted out by an eluent EA:PE=1:10, and then target compounds were eluted out by EA:PE=1:2). 255 mg of yellow solid was obtained. MS m/z: 570.7 (M+1)$^+$. $^1$H-NMR (400 MHz, DMSO-d$_6$) δ: 11.50 (s, 1H), 8.90 (s, 1H), 8.64 (s, 1H), 7.77 (d, J=8.7 Hz, 2H), 7.51 (t, J=5.7 Hz, 1H), 7.15 (t, J=8.7 Hz, 1H), 7.08 (dd, J=6.0, 2.2 Hz, 1H), 6.75 (ddd, J=11.3, 8.1, 5.8 Hz, 3H), 6.27 (t, J=6.0 Hz, 1H), 3.37 (q, J=6.7 Hz, 2H), 3.10 (q, 2H), 3.05 (s, 6H).

Embodiment 11 Synthesis of Compound of Formula II-7

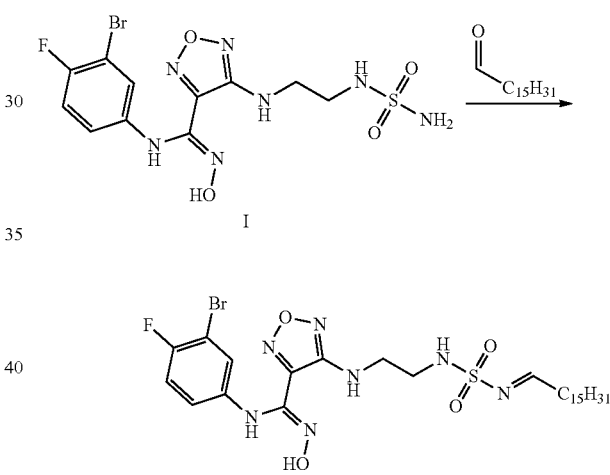

400 mg (0.92 mmol) of compound of Formula I and 2.4 g (10.0 mmol) of palmital were added into a reaction bottle. 10 mL of acetonitrile was added. Stirring was performed for reaction for 1 h at a room temperature. TLC was adopted for monitoring the reaction (EA:PE=1:1). The reaction was completed. A temperature of reaction liquid was lowered to a room temperature. The reaction liquid was cooled into solid. Ethyl acetate was added for dissolving the solid. Silica gel was added for sample mixing. Products were separated by column chromatography (raw material aldehyde was firstly eluted out by an eluent EA:PE=1:10, and then target compounds were eluted out by EA:PE=1:2). 208 mg of yellow solid was obtained. MS m/z: 661.6 (M+1)$^+$. $^1$H NMR (400 MHz, DMSO-d$_6$) δ: 11.52 (s, 1H), 8.83 (s, 1H), 7.33 (s, 1H), 7.20 (s, 1H), 7.10 (dd, J=6.1, 2.7 Hz, 1H), 6.78 (m, 1H), 6.70 (s, 1H), 6.22 (t, J=6.0 Hz, 1H), 3.18 (m, 2H), 3.10 (m, 2H), 1.68-1.64 (m, 2H), 1.45-1.31 (m, 26H), 0.89 (t, J=6.2 Hz, 3H).

Embodiment 12 Synthesis of Compound of Formula II-8

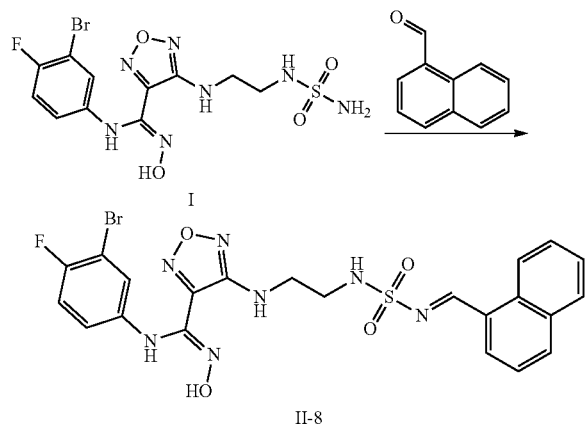

400 mg (0.92 mmol) of compound of Formula I and 0.94 g (6.0 mmol) of 1-formyl naphthalene were added into a reaction bottle. 10 mL of acetonitrile was added. Stirring was started. A temperature was raised to 60° C. Reaction was performed for 1 h. TLC was adopted for monitoring the reaction (EA:PE=1:1). The reaction was completed. A temperature of reaction liquid was lowered to a room temperature. The reaction liquid was cooled into solid. Ethyl acetate was added for dissolving the solid. Silica gel was added for sample mixing. Products were separated by column chromatography (raw material aldehyde was firstly eluted out by an eluent EA:PE=1:10, and then target compounds were eluted out by EA:PE=1:2). 305 mg of yellow solid was obtained. MS m/z: 577.7 (M+1)+. $^1$H-NMR (400 MHz, DMSO-$d_6$) δ: 11.50 (s, 1H), 9.39 (s, 1H), 9.10 (d, J=8.4 Hz, 1H), 8.90 (s, 1H), 8.29 (d, J=7.7 Hz, 2H), 8.10 (d, J=8.0 Hz, 1H). 7.99 (t, J=5.6 Hz, 1H), 7.77~7.62 (m, 3H), 7.14 (t, J=8.8 Hz, 1H), 7.09 (dd, J=5.9, 2.4 Hz, 1H), 6.77~6.70 (m, 1H), 6.34 (t, J=5.9 Hz, 1H), 3.42 (q, J=12.6, 6.4 Hz, 2H), 3.24 (q, J=6.0 Hz, 2H).

Embodiment 13 Synthesis of Compound of Formula II-9

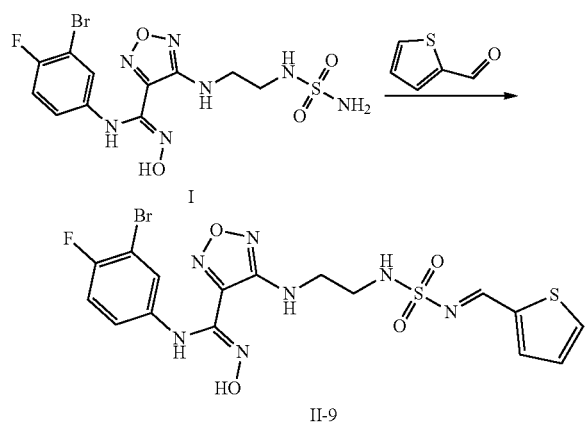

400 mg (0.92 mmol) of compound of Formula I and 0.72 g (6.42 mmol) of 2-thenaldehyde were added into a reaction bottle. Stirring was started. A temperature was raised to 110° C. Reaction was performed for 1 h. TLC was adopted for monitoring the reaction (EA:PE=1:1). The reaction was completed. A temperature of reaction liquid was lowered to a room temperature. The reaction liquid was cooled into solid. Ethyl acetate was added for dissolving the solid. Silica gel was added for sample mixing. Products were separated by column chromatography (raw material aldehyde was firstly eluted out by an eluent EA:PE=1:10, and then target compounds were eluted out by EA:PE=1:2). 280 mg of yellow solid was obtained. MS m/z: 533.6 (M+1)+. $^1$H-NMR (400 MHz, DMSO-$d_6$) δ: 11.50 (s, 1H), 9.07 (s, 1H), 8.90 (s, 1H), 8.10 (dd, J=16.7, 4.1 Hz, 2H), 7.84 (s, 1H), 7.33 (t, J=4.1 Hz, 1H), 7.21~7.05 (m, 2H), 6.81~6.70 (m, 1H), 6.30 (t, J=5.9 Hz, 1H), 3.37 (d, J=6.4 Hz, 2H), 3.11 (dd, J=11.3, 5.8 Hz, 2H).

Embodiment 14 In Vitro Plasma Experiment of Target Compounds 6.1 Determination Conditions of High Performance Liquid Chromatography Liquid chromatograph: Waters 2489UV/Visible Detector, Waters 1525Binary HPLC Pump.

Chromatographic column: Kromasil 100-5-C18, Dim: 4.6×150 mm, Part/Serial: M05CLA15/E121514.

Mobile phase: acetonitrile (50% to 80%) and water gradient elution.

Flow rate: 1 mL/min at a column temperature of 25° C.

Detection wavelength: 254 nm at a sample size of 10 μL.

Under the condition of no mobile phase interference, the Epacadostat retention time was about 20 min.

6.2 Sample Preparation

The target compounds were dissolved into a DMSO solvent. The concentration was converted into Epacadostat 120 mg/mL according to the concentration. 20 μL of the solution was taken and added into 1.18 mL of fresh rat blank plasma, and incubation was performed at 37° C. to obtain a sample.

6.3 Sample Pretreatment

120 μL of the sample was precisely sucked at a specified time point each time. 120 μL of acetonitrile was added. High-speed vortex mixing was performed for 2 min. Centrifugation was performed at 10000 r/min for 15 min. Supernatant was taken and filtered by a 13 mm 0.45 μm filter membrane, and then determination could be performed.

6.4 Original Drug Epacadostat Plasma Stability Test

20 μL of DMSO solution (120 mg/mL) of Epacadostat was taken and added into 1.18 mL of fresh rat blank plasma. Incubation was performed at 37° C. 120 μL of sample was taken at different time points respectively. Sample pretreatment was performed according to the method of 6.3. Determination was performed by an HPLC method. A peak area was recorded, and a drug concentration was calculated. The results are as shown in Table 4.

TABLE 4

| | Time/h | | | |
|---|---|---|---|---|
| | 1 | 3 | 6 | 24 |
| Epacadostat concentration in plasma (mg/mL) | 1.22 | 1.20 | 1.24 | 1.20 |

Data in Table 4 show that the Epacadostat can stably exist in the plasma.

6.5 In Vitro Plasma Conversion Experiment of Target Compounds

According to the method of 6.4, we performed in vitro plasma conversion experiment on the target compounds to test conversion rates of the compounds II-5 to II-9 converted into the Epacadostat at different time points. The results are as shown in Table 5.

TABLE 5

| Compound | Conversion rate at different time points (%) | | | | | |
|---|---|---|---|---|---|---|
| | 0.5 h | 1 h | 2 h | 3 h | 6 h | 12 h |
| II-5 | 59.8 | 64.8 | 65.5 | 72.4 | 88.8 | 98.9 |
| II-6 | 46.2 | 5.3 | 67.9 | 87.2 | 91.0 | 100 |
| II-7 | 42.8 | 50.4 | 59.9 | 66.2 | 87.9 | 97.8 |
| II-8 | 38.4 | 44.7 | 54.1 | 64.7 | 79.2 | 96.7 |
| II-9 | 47.2 | 49.0 | 51.6 | 75.2 | 89.6 | 100 |

The data above show that all of the target compounds can be fast converted into original drug Epacadostat in the plasma.

Embodiment 15 Rat In Vivo Pharmacokinetic Experiment 15 healthy SD male rats with the body weight in a range of 200 to 220 g were taken, and were regularly fed with rat standard formula granulated feed every day. Fasting was performed for 12 h before the experiment. Feeding was resumed after 4 h after administration. Free water drinking was allowed before, after and during the experiment. The rats were randomly divided into 6 groups. The first group was feed with Epacadostat at single dose. The second to sixth groups were fed with compounds prepared according to Embodiment 9 to Embodiment 13 at single dose. The molar concentration of Epacadostat in the dosage of administration of the 6 groups of rats was 10 mg/kg. 0.2 to 0.3 mL of blood was taken from fundus venous plexus before administration (at 0 h), and 0.5, 1, 2, 4, 6, 8, 10, 24 and 48 h after administration respectively. Heparin anticoagulation was performed. The plasma was separated through centrifugation. 0.1 mL of plasma was accurately measured and added into an EP tube. 1.2 mL of ethyl acetate was added. High-speed uniform mixing was performed by a vortex mixer for 5 min. Centrifugation was performed for 5 min (8000 r/min). Supernatant was collected. A solvent was blown dry by nitrogen gas on a pressure blowing concentrator at 30° C. Residues were dissolved by 100 μL of mobile phase. High-speed uniform mixing was performed by a vortex mixer for 10 min. Centrifugation was performed for 5 min (14000 r/min). 80 μL of supernatant was transferred into a sample bottle. 10 μL of the sample was detected through HPLC. A chromatogram map was recorded. The results are as shown in Table 6:

TABLE 6

| Compound | Oral bioavailability (AUC, μL · h) |
|---|---|
| Epacadostat | 15.1 |
| II-5 | 16.5 |
| II-6 | 15.9 |
| II-7 | 16.4 |
| II-8 | 17.4 |
| II-9 | 16.1 |

In vivo and in vitro pharmacological experiments show that the 1,2,5-oxadiazole derivative obtained by the design method of the present invention has good bioavailability, is superior to the Epacadostat, and has further clinic study potentials as a novel IDO inhibitor.

The foregoing descriptions are merely implementations of the present invention, and it should be noted that, a person skilled in the art may further make several improvements and modifications without departing from the principle of the present invention. These improvements and modifications shall all fall within the protection scope of the present invention

What is claimed is:

1. A compound of Formula I and Formula II, a stereoisomer thereof, a pharmaceutically acceptable salt or a pharmaceutically acceptable solvate thereof:

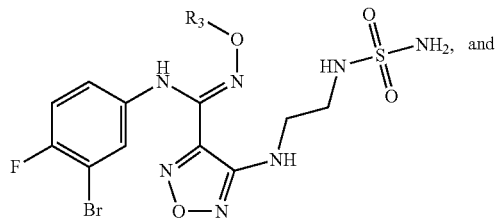

Formula I

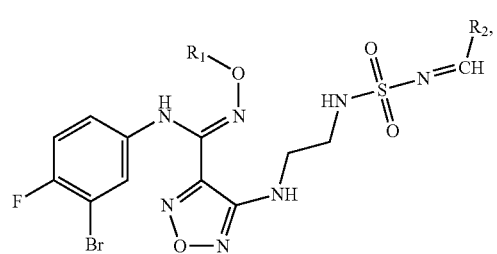

Formula II wherein $R_1$ is H, —C(═O) Ra, —C(═C) $OR_b$, —C(═O) CnPhR$_c$, or —P(═O) ($OR_d$)($OR_e$), where Ra is C1-C18 alkyl, haloalkyl, carboxyl or cyanogroup substituted alkyl, Rb is C1-C18 alkyl, haloalkyl, or carboxyl and cyanogroup substituted alkyl, Rc is C1-C1 alkyl, haloalkyl, H or halogen, Rd and Re are each independently hydrogen, C1-C16 saturated or unsaturated chain hydrocarbyl, C1-C16 saturated or unsaturated cyclohydrocarbyl, substituted or unsubstituted aromatic ring, or substituted or unsubstituted heteroaromatic ring, where the substituent on the ring is halogen, nitryl, cyanogroup, hydroxyl, amino group, C1-C16 alkyl or C1-C16 alkoxy, and n is 0 or 1;

$R_2$ is hydrogen, substituted or unsubstituted $C_1$-$C_{10}$ alkyl, substituted or unsubstituted $C_3$-$C_{10}$ cycloalkyl, substituted or unsubstituted $C_2$-$C_{10}$ alkenyl, substituted or unsubstituted $C_1$-$C_{20}$ alkynyl, substituted or unsubstituted $C_5$-$C_{20}$ aryl, or substituted or unsubstituted $C_3$-$C_{14}$ heteroaryl, wherein heteroatoms may be S, O, NH or NR$_f$; where R$_f$ and the "substituted" refer to having one or more substituents selected from the group consisting of: halogen, hydroxyl, —NH$_2$, nitryl, substituted or unsubstituted $C_1$-$C_{10}$ alkyl, substituted or unsubstituted $C_1$-$C_{10}$ haloalkyl, substituted or unsubstituted $C_1$-$C_{10}$ alkoxy, substituted or unsubstituted $C_2$-$C_{10}$ cycloalkyl, substituted or unsubstituted $C_2$-$C_{10}$ alkenyl, substituted or unsubstituted $C_3$-$C_{10}$ alkynyl, substituted or unsubstituted $C_5$-$C_{20}$ aryl, and substituted or unsubstituted $C_3$-$C_{14}$ heteroaryl, wherein heteroatoms may be S, O or NH;

$R_3$ is —C(=O)$R_a$, —C(=O)O$R_b$, —C(=O)CnPh$R_c$, or —P(=O) (O$R_d$)(O$R_e$) where $R_a$ is C9-C18 alkyl, haloalkyl, or carboxyl and cyanogroup substituted alkyl, Rb is C9-C18 alkyl, haloalkyl, or carboxyl and cyanogroup substituted alkyl, Rc is C1-C18 alkyl, haloalkyl, H or halogen; Rd and Re are each independently hydrogen, C1-C16 saturated or unsaturated chain hydrocarbyl, C1-C16 saturated or unsaturated cyclohydrocarbyl, substituted or unsubstituted aromatic ring, or substituted or unsubstituted heteroaromatic ring, wherein the substituent on the ring is halogen, nitryl, cyanogroup, hydroxyl, amino group, C1-C16 alkyl or C1-C16 alkoxy; and n is 0 or 1.

2. A The compound of Formula I or Formula II, the stereoisomer thereof, the pharmaceutically acceptable salt or the pharmaceutically acceptable solvate thereof according to claim 1, wherein the compound of Formula I is:

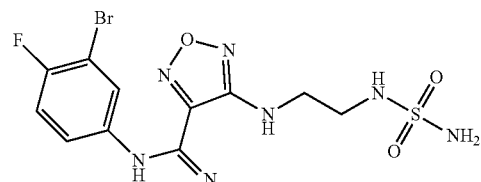

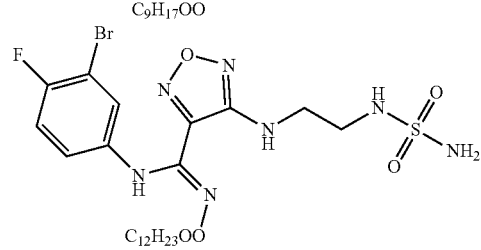

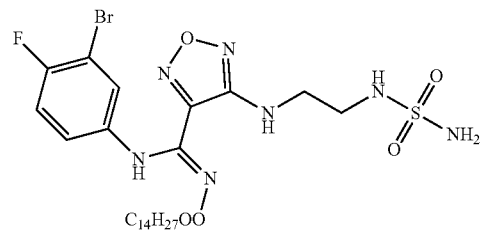

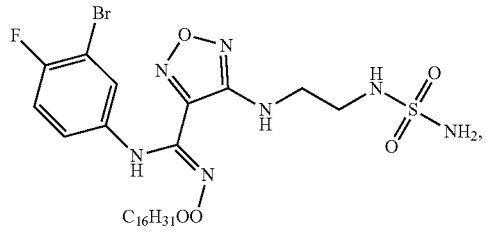

and the compound of Formula II is selected from:

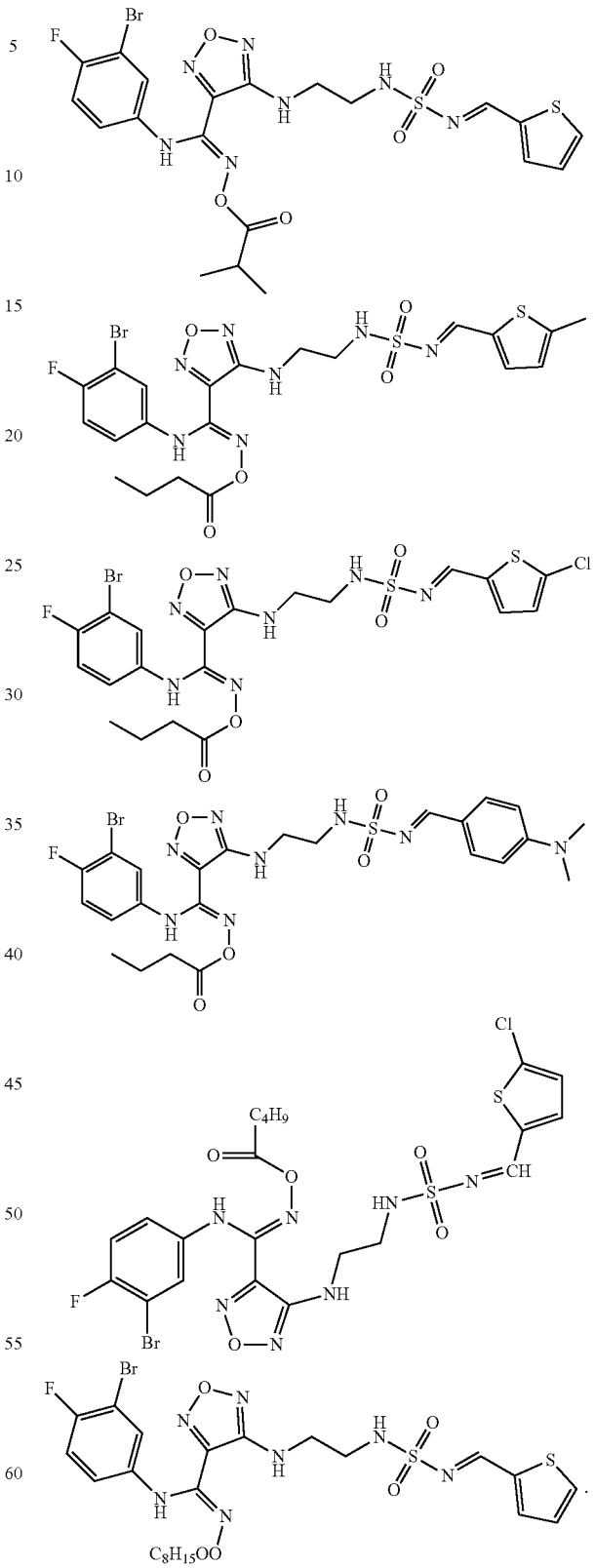

3. The compound of Formula I or Formula II, the stereoisomer thereof, the pharmaceutically acceptable salt or the pharmaceutically acceptable solvate thereof according to claim 1, wherein the compound of Formula II is:

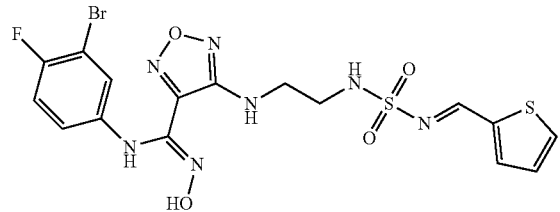

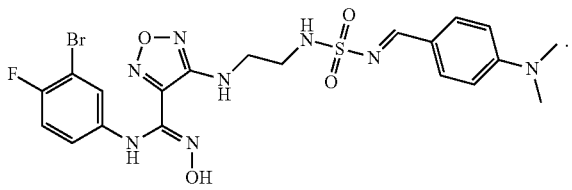

4. A method of preparing compounds of Formula I and Formula II, carried out through the following reactions:

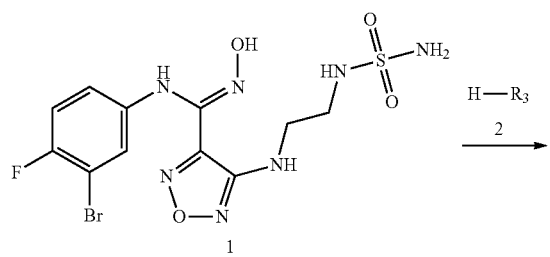

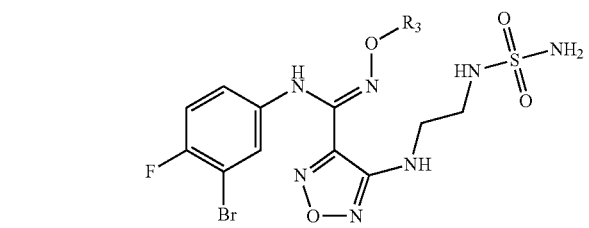

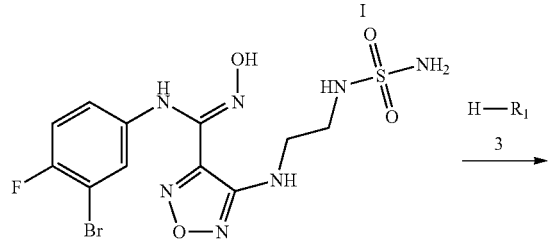

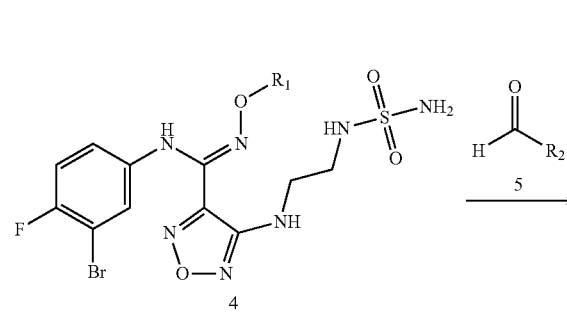

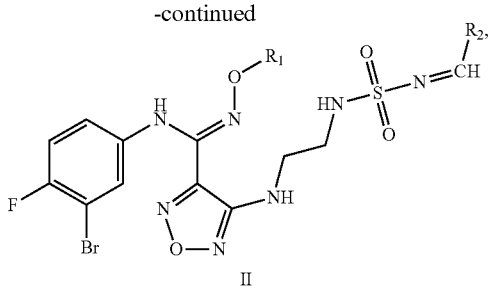

II wherein in the reaction, a compound 1 and a compound 2 are prepared into the compound of Formula I through a condensation dehydration reaction under room temperature or heating condition in the absence of a solvent or an organic solvent, the compound 1 and a compound 3 are prepared into a compound of Formula 4 through a condensation dehydration reaction under room temperature or heating condition in the absence of a solvent or an organic solvent, and the compound 4 and a compound 5 are prepared into a compound of Formula II through a condensation dehydration reaction under room temperature or heating condition in the absence of a solvent or an organic solvent, wherein $R_1$ is H, —C(=O) Ra, —C(=O) OR$_b$, —C(=O) CnPhR$_c$, or —P(=O) (OR$_d$)(OR$_e$), where Ra is C1-C18 alkyl, haloalkyl, carboxyl or cyanogroup substituted alkyl, Rb is C1-C18 alkyl, haloalkyl, or carboxyl and cyanogroup substituted alkyl, Rc is C1-C18 alkyl, haloalkyl, H or halogen, Rd and Re are each independently hydrogen, C1-C16 saturated or unsaturated chain hydrocarbyl, C1-C16 saturated or unsaturated cyclohydrocarbyl, substituted or unsubstituted aromatic ring, or substituted or unsubstituted heteroaromatic ring, where the substituent on the ring is halogen, nitryl, cyanogroup, hydroxyl, amino group, C1-C16 alkyl or C1-C16 alkoxy, and n is 0 or 1;

$R_2$ is hydrogen, substituted or unsubstituted $C_1$-$C_{10}$ alkyl, substituted or unsubstituted $C_3$-$C_{10}$ cycloalkyl, substituted or unsubstituted $C_2$-$C_{10}$ alkenyl, substituted or unsubstituted $C_3$-$C_{10}$ alkynyl, substituted or unsubstituted $C_5$-$C_{20}$ aryl, or substituted or unsubstituted $C_3$-$C_{14}$ heteroaryl, wherein heteroatoms may be S, O, NH or NR$_f$; where R$_f$ and the "substituted" refer to having one or more substituents selected from the group consisting of: halogen, hydroxyl, —NH$_2$, nitryl, —CN, substituted or unsubstituted $C_1$-$C_{10}$ alkyl, substituted or unsubstituted $C_1$-$C_{10}$ haloalkyl, substituted or unsubstituted $C_1$-$C_{10}$ alkoxy, substituted or unsubstituted $C_1$-$C_{10}$ cycloalkyl, substituted or unsubstituted $C_2$-$C_{10}$ alkenyl, substituted or unsubstituted $C_3$-$C_{10}$ alkynyl, substituted or unsubstituted $C_5$-$C_{20}$ aryl, and substituted or unsubstituted $C_3$-$C_{14}$ heteroaryl, wherein heteroatoms may be S, O or NH;

$R_3$ is —C(=O) R$_a$, —C(=O)OR$_b$, —C(=O)CnPhR$_c$, or —P(=O) (OR$_d$)(OR$_e$) where Ra is C9-C18 alkyl, haloalkyl, or carboxyl and cyano group substituted alkyl, Rb is C9-C18 alkyl, haloalkyl, or carboxyl and cyano group substituted alkyl, Rc is C1-C18 alkyl, haloalkyl, H or halogen; Rd and Re are each independently hydrogen, C1-C16 saturated or unsaturated chain hydrocarbyl, C1-C16 saturated or unsaturated cyclohydrocarbyl, substituted or unsubstituted aromatic ring, or substituted or unsubstituted heteroaromatic ring, wherein the substituent on the ring is halogen, nitryl, cyano group, hydroxyl, amino group, C1-C16 alkyl or C1-C16 alkoxy; and n is 0 or 1.

5. The method according to claim 4, wherein the solvent comprises one or more of methyl alcohol, ethyl alcohol, dichloromethane, trichloromethane, acetonitrile, DMF, DMA, DMSO, THF or toluene.

6. The method according to claim 4, wherein the reaction temperature ranges from 0° C. to 200° C.

7. A pharmaceutical composition, comprising the compound of Formula I and/or Formula II, the stereoisomer thereof, the pharmaceutically acceptable salt or the pharmaceutically acceptable solvate thereof according to claim 1, and a pharmaceutically acceptable carrier and/or auxiliary agent.

8. A method for treating indoleamine-(2,3)-dioxygenase-mediated disease in a subject comprising administering to the subject the compound of claim 1, wherein the indoleamine-(2,3)-dioxygenase-mediated disease is cervical cancer, ovarian cancer, carcinoma tubae, peritonealcancer, non-small cell lung cancer, triple negative breast cancer, or urothelial cancer.

9. A method of inhibiting indoleamine-(2,3)-dioxygenase comprising contacting indoleamine-(2,3)-dioxygenase the with the compound of claim 1.

10. A method of reducing inflammation in a subject comprising administering to the subject the compound of claim 1.

* * * * *